United States Patent
Cockburn et al.

(10) Patent No.: US 7,875,025 B2
(45) Date of Patent: Jan. 25, 2011

(54) ELECTRO-SURGICAL NEEDLE APPARATUS

(75) Inventors: John Francis Cockburn, Norfolk (GB); Donald James Alexander Cockburn, County Dublin (IE); Simon Wemyss-Holden, Norfolk (GB)

(73) Assignee: Instrumedical Ltd., Norfolk (GB)

( * ) Notice: Subject to any disclaimer, the term of this patent is extended or adjusted under 35 U.S.C. 154(b) by 1017 days.

(21) Appl. No.: 11/348,541

(22) Filed: Feb. 6, 2006

(65) Prior Publication Data

US 2006/0217704 A1    Sep. 28, 2006

(30) Foreign Application Priority Data

Feb. 4, 2005    (GB)    ................. 0502384.1

(51) Int. Cl.
*A61B 18/14*    (2006.01)
(52) U.S. Cl. .................. 606/41; 606/32; 606/34
(58) Field of Classification Search ........... 606/41, 606/32–34, 48–50; 607/101–102, 115–116; 340/635–636.16, 660–663
See application file for complete search history.

(56) References Cited

U.S. PATENT DOCUMENTS

| | | | | |
|---|---|---|---|---|
| 4,494,539 A | * | 1/1985 | Zenitani et al. | ............... 606/33 |
| 5,328,453 A | * | 7/1994 | Sibalis | ................ 604/20 |
| 5,419,344 A | | 5/1995 | DeWitt | |
| 5,476,481 A | * | 12/1995 | Schondorf | ............... 607/2 |
| 5,536,267 A | * | 7/1996 | Edwards et al. | ............... 606/41 |
| 5,567,413 A | * | 10/1996 | Klaveness et al. | .......... 424/9.51 |
| 5,702,359 A | * | 12/1997 | Hofmann et al. | .............. 604/20 |
| 5,800,484 A | * | 9/1998 | Gough et al. | ................ 607/104 |

(Continued)

FOREIGN PATENT DOCUMENTS

WO     03/026525     4/2003

(Continued)

OTHER PUBLICATIONS

Vijh, A.K. "Electrochemical field effects in biological materials: electro-osmotic dewatering of cancerous tissue as the mechanistic proposal for the electrochemical treatment of tumors." Journal of Materials Science: Materials in Medicine 10 (1999) pp. 419-423.

(Continued)

*Primary Examiner*—Linda C Dvorak
*Assistant Examiner*—Amanda Scott
(74) *Attorney, Agent, or Firm*—Ladas & Parry LLP

(57) ABSTRACT

A needle assembly (N) for RF ablation of target tissue in e.g. the liver (L) of a patient comprises a radial array of electrodes (1) in the form of loops which can be expanded by feeding the proximal ends of the Y electrodes along the bore of the needle assembly. An RF power supply (2) is connection between the array of electrodes and a skin pad (P) in contact with the skin (S) of a patient and, in accordance with the invention, is biased by a DC power supply 4 which generates electro-osmotic and/or electrolytic effects in the target tissue. In particular, chloride ions are discharged to generate chlorine which has a potent cytocidal effect and water can be attracted to the array of electrodes by electro-osmosis, thereby alleviating the problems of low electrical and thermal conductivity encountered with conventional apparatus.

29 Claims, 5 Drawing Sheets

U.S. PATENT DOCUMENTS

| | | | |
|---|---|---|---|
| 5,827,276 A * | 10/1998 | LeVeen et al. | 606/41 |
| 5,855,576 A * | 1/1999 | LeVeen et al. | 606/41 |
| 5,857,992 A * | 1/1999 | Haak et al. | 604/20 |
| 5,873,849 A * | 2/1999 | Bernard | 604/20 |
| 5,993,434 A * | 11/1999 | Dev et al. | 604/501 |
| 6,258,086 B1 * | 7/2001 | Ashley et al. | 606/41 |
| 6,278,895 B1 * | 8/2001 | Bernard | 604/20 |
| 6,418,341 B1 * | 7/2002 | Hofmann et al. | 604/21 |
| 6,889,089 B2 * | 5/2005 | Behl et al. | 607/99 |
| 7,025,767 B2 * | 4/2006 | Schaefer et al. | 606/41 |
| 7,113,821 B1 * | 9/2006 | Sun et al. | 604/21 |
| 7,182,761 B2 * | 2/2007 | Garabedian et al. | 606/41 |
| 7,306,595 B2 * | 12/2007 | Ostrovsky et al. | 606/41 |
| 7,309,336 B2 * | 12/2007 | Ashley et al. | 606/41 |
| 7,344,518 B2 * | 3/2008 | McGuckin et al. | 604/164.01 |
| 7,344,533 B2 * | 3/2008 | Pearson et al. | 606/41 |
| 7,412,285 B2 * | 8/2008 | Schroeppel et al. | 607/2 |
| 7,419,487 B2 * | 9/2008 | Johnson et al. | 606/41 |
| 7,431,720 B2 * | 10/2008 | Pendekanti et al. | 606/41 |
| 7,447,551 B2 * | 11/2008 | Kuo et al. | 607/152 |
| 2001/0001819 A1 * | 5/2001 | Lee et al. | 606/41 |
| 2001/0012956 A1 * | 8/2001 | Behl et al. | 607/99 |
| 2002/0087112 A1 * | 7/2002 | Constantz et al. | 604/22 |
| 2002/0103515 A1 | 8/2002 | Davey et al. | |
| 2003/0083681 A1 * | 5/2003 | Moutafis et al. | 606/167 |
| 2003/0125660 A1 * | 7/2003 | Moutafis et al. | 604/22 |
| 2004/0025556 A1 * | 2/2004 | Klint et al. | 72/130 |
| 2004/0143259 A1 | 7/2004 | Mulier et al. | |
| 2004/0236320 A1 * | 11/2004 | Protsenko et al. | 606/32 |
| 2005/0165393 A1 * | 7/2005 | Eppstein | 606/41 |
| 2005/0182449 A1 * | 8/2005 | Auge et al. | 607/3 |
| 2005/0197571 A1 * | 9/2005 | McVeigh | 600/437 |
| 2005/0222646 A1 * | 10/2005 | Kroll et al. | 607/72 |
| 2006/0058602 A1 * | 3/2006 | Kwiatkowski et al. | 600/407 |
| 2006/0111705 A1 * | 5/2006 | Janzen et al. | 606/41 |

FOREIGN PATENT DOCUMENTS

WO    WO 03026525 A1 *    4/2003

OTHER PUBLICATIONS

J.F. Cockburn et al., Bimodal Electric Tissue Ablation (Beta)—In Viv Evaluation of the Effect of Applying Direct Current Before and During Radiofrequency Ablation of Porcine Liver(2007) 62, pp. 213-220.

Christopher Dobbins et al., Bimodal Electric Tissue Ablation-Modified Radiofrequency Ablation With a Le Veen Electrode in a Pig Model; Journal of Sugical Research 144, (2008) pp. 111-116.

* cited by examiner

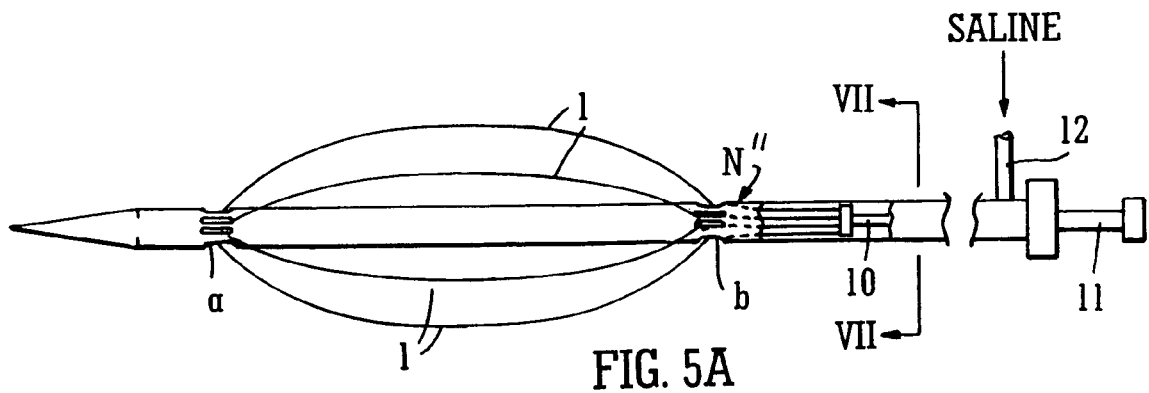
FIG. 5A
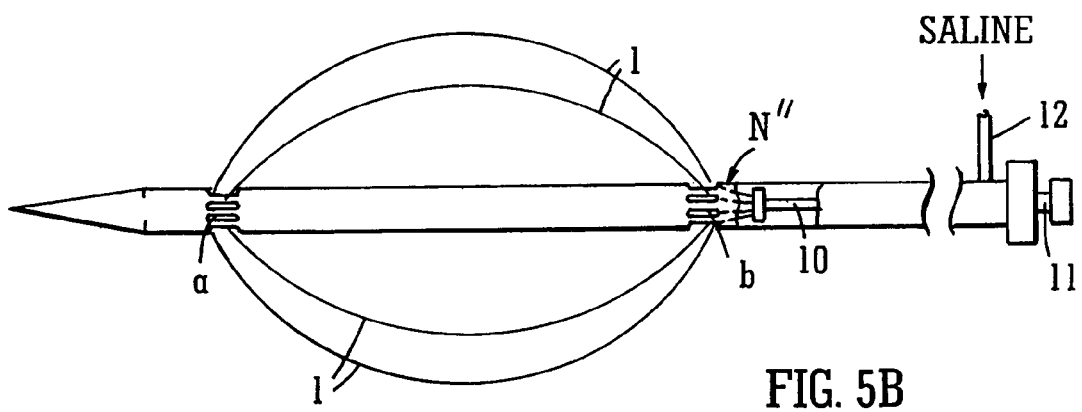
FIG. 5B
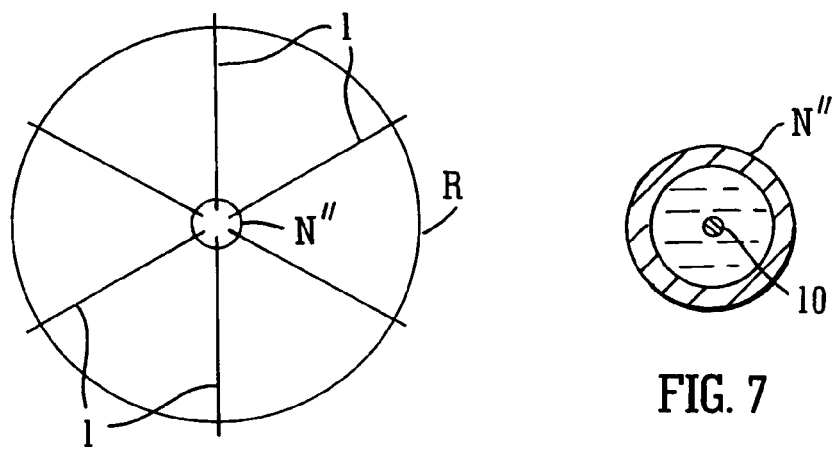
FIG. 6
FIG. 7

ELECTRO-SURGICAL NEEDLE APPARATUS

The present invention relates to surgical apparatus for treating tumours in internal organs or bones of the human body, the apparatus comprising a penetrative needle assembly for penetrating into and devitalising target tissue in a region around the needle assembly. The target tissue may be a tumour in e.g. the liver, the breast, the brain, bones, the kidney or the lung.

Such apparatus is known e.g. from U.S. Pat. No. 5,827,276 (LeVeen et al), US 2004/133196 (which concerns a development to the LeVeen needle) and WO 03/026525 (RITA Medical Systems Inc.), all of which are incorporated herein by reference. The needle arrangements disclosed in the above specifications necrotize the target tissue by radiofrequency ablation which heats the target tissue to a temperature of between 60 and 100° C., resulting in cell death. The dead cells are subsequently gradually reabsorbed by natural processes within the patient's body.

Another application of RF treatment is disclosed in U.S. Pat. No. 5,419,344 which is concerned with hair removal in the treatment of folliculitis barbae ("razor bumps"). A thin probe is inserted into a hair follicle and "DC electrolysis" and "RF thermolysis" circuits are connected directly between the probe and a "ground device" held by the patient. The circuitry is unclear and no details of the power of either circuit are given. However the "RF thermolysis" circuit apparently heats and softens the tissue and it is stated that sodium hydroxide generated by electrolysis in the follicle enables the hair to be withdrawn. The rate of reaction is increased by the heating effect. There is no disclosure of ablation, i.e. tissue destruction.

Typically the power level employed in radiofrequency ablation is up to about 200 W at a frequency of typically 460 or 480 kHz.

Other literature references suggest powers of about 20 W and frequencies of 460 kHz or 480 kHz.

It will be apparent that the RF power generated in the DeWitt apparatus is considerably below such levels, since only mild heating of a hair follicle is involved.

It should be noted however that in principle, a variety of energy transfer means may be employed to ablate the target tissue, either by heating or by cooling. The following modes of energy transfer are disclosed in WO 03/026525:

(i) a microwave power source coupled to a microwave antenna providing microwave energy in the frequency range from about 915 MHz to about 2.45 GHz;
(ii) a radio-frequency (RF) power source coupled to an RF electrode;
(iii) a coherent light source coupled to an optical fiber or light pipe;
(iv) an incoherent light source coupled to an optical fiber;
(v) a heated fluid coupled to a catheter with a closed or at least partially open lumen configured to received the heated fluid;
(vi) a cooled fluid coupled to a catheter with a closed or at least partially open lumen configured to receive the cooled fluid;
vii) a cryogenic fluid;
(viii) a resistive heating source coupled to ac conductive wire;
(ix) an ultrasound power source coupled to an ultrasound emitter, wherein the ultrasound power source produces ultrasound energy in the range of about 300 kHz to about 3 GHz;
(x) and combinations thereof.

In principle all the above modes of energy transfer can be used for tumour ablation in the apparatus of the present invention.

The LeVeen needle electrode is currently on the market and available from Boston Scientific Corporation and comprises a cannula having ten flexible tines disposed therein and deployable from a distal end of the cannula. The tines curve radially outwardly in an umbrella configuration when deployed and penetrate into a tumour. The electrodes are coupled to an RF power supply and distribute the RF energy into the tumour. As a result, tumour tissue in a roughly spherical region several centimeters in diameter is destroyed.

Nevertheless there is a need to increase the kill radius and in particular to kill target tissue at a larger distance from the individual electrode tines, without employing excessive power. One of the problems which arises in RF ablation is a drop in thermal conductivity of the tissue as it is necrotized, particularly as a result of charring of the tissue, complicated by changes in impedance of the tissue and hence changes in the heating effect of the RF energy. A further problem which arises in the above prior art apparatus is the need to connect one pole of the RF power supply to the patient's body in order in order to provide a complete circuit, normally via a conductive pad applied to the skin. This requirement tends to limit the power which can safely be employed.

In an attempt to overcome or alleviate the above problems, US 2004/0143259A (Mulier) discloses a needle apparatus in which conductive fluid (e.g. saline solution) is introduced from two spaced apart distal regions of a needle assembly in the vicinity of two RF electrodes to provide what are referred to as "virtual electrodes" constituted by the bodies of liquid permeating into the tissue. RF power is conducted through the region of tissue lying between these two bodies of liquid. Suction is applied from an intermediate region of the needle to remove the saline solution.

However there remains a pressing need for improvements in the effectiveness of the above apparatus.

For example another problem arises when blood vessels adjacent to the tumour act as a sump, carrying heat away from the treated tissue and preventing adequate devitalisation. This failure to obliterate tumor tissue is a well-recognised cause of patient death. Increasing the radiofrequency power adjacent to a blood vessel can overcome this problem, but at a cost: occlusion of or damage to the blood vessel.

On occasion this may lead to unwanted reduction in blood supply and consequent organ failure.

Another undesirable feature of radiofrequency and other existing forms of ablation is the reliance on completing the ablation in a short period of time: typically an hour or so in a sedated patient having a percutaneous procedure or several hours in a patient having synchronous surgery under general anaesthetic. Reliance on rapid tissue necrosis can be a considerable insult to the body and has been shown to cause "systemic inflammatory reaction syndrome" wherein the patient becomes febrile, tachycardic, sweaty and unwell, requiring a longer hospital stay. Abscess formation is a potential complication of this process.

The present invention provides surgical apparatus for treating tumours in internal organs or bones of the human body. The apparatus comprising a penetrative needle assembly for penetrating into tumour tissue, energy transfer means coupled to the needle assembly and arranged in use to ablate target tissue in a region around the needle assembly and at least one cathode arranged in use to induce electro-endosmosis and optionally electrolysis in target tissue in said region.

Preferably said energy transfer means comprises an AC source coupled to said cathode and arranged to generate RF ablation in said region, said AC source being arranged to generate a power of at least 5 W, more preferably at least 10 W, most preferably at least 20 W.

The opposite pole of the DC source can be connected to a large conductive pad in contact with the patient's skin or preferably (in order to avoid the risk of skin burns) can instead be connected to a further electrode (e.g. in the form of a needle) inserted separately into the patient's body tissue or can be connected to or inserted through e.g. a cannula of the needle assembly through which the cathode extends. A sleeve or internal coating of PTFE or other insulating material can be provided within the lumen of the cannula to insulate the cathode from the cannula.

In a preferred embodiment the apparatus of the invention further comprises an anode arranged to be inserted into the patient's body tissue.

Preferably said anode is in the form of a needle.

In one embodiment the energy transfer means comprises an AC source coupled to said electrode. The combined effect of heating and electro-osmosis in the target tissue increases the effectiveness of the apparatus. In particular the negative potential of the cathode will attract water in the target tissue to the region of necrosis around the electrode and tends to raise both the thermal and the electrical conductivity. This tends to increase the volume of the region of tissue necrosis around the needle assembly, i.e. it enables larger tumours to be treated using a given power.

Accordingly, the apparatus of the invention preferably comprises a DC source arranged to bias said cathode to a negative potential. Preferably said negative potential is in the range −9V to −12V relative to the positive pole of said DC source.

Another feature of existing radiofrequency, cryogenic and similar ablative methods is their need to transfer energy to (or from) the entire volume of tissue which is to be necrotised.

In a preferred embodiment of the present invention, the needle apparatus comprises an extendable electrode array which is deployable to enclose a volume of tumour tissue and is arranged in use to electrolyse selectively the periphery of the enclosed volume. By applying high energy alternating current at radiofrequency in a cutting diathermy mode, the extendable electrode array can expand to its desired shape such that the electrodes surround the tumour. Following this, supplementary electrolysis, ablative RF, or other ablation treatment can be delivered as required. This typically will result in a shell of coagulative necrosis at the periphery of the enclosed volume which will isolate tumour tissue within the interior of the enclosed volume from its supply of blood or other nutrients. Hence the interior tumour tissue will also die, even if it is not ablated. Repair or regrowth of nutrient channels can be prevented by continued application of DC.

In another aspect the invention provides surgical apparatus for necrotizing target tissue in bones or in internal organs of the human body, the apparatus comprising at least one penetrative anode arranged in use to penetrate into and induce electrolysis in said target tissue.

One advantage of an embodiment of the present invention that generates electrolysis is that electrolysis can devitalise tissue right up to a blood vessel wall. This arises from the electrically insulating properties of the walls of blood vessels. Furthermore, for this reason blood vessels can be left intact by such apparatus, which can be advantageous e.g. in a situation of liver cirrhosis where it is important to preserve blood supply to non-cancerous liver.

The principles of operation of two preferred embodiments of the invention into different aspects are described below.

FIG. 1 is a purely schematic diagram showing a penetration anode 1 inserted in the liver L of a patient. Chloride ions (either naturally present in the body fluid or provided by injecting saline solution in the vicinity of the anode) are discharged and have a potent cytocidal effect in a region R1 surrounding the anode. The anode 1 is connected to the positive pole of a DC power supply (not shown) whose negative pole is connected to a cathode (not shown) inserted into body tissue or in contact with the patient's skin.

The bubbles B of chlorine gas surrounding the anode 1 can be detected by ultrasonic imaging, either B-mode (because the bubbles have distinctly different sonic impedance from the surrounding tissue) or Doppler ultrasound (because the bubbles are moving). In principle, a cathode could be inserted in the liver or could be provided in the form of a conductive pad in contact with the exterior of the patient's body, for example.

Apart from the discharge of chloride ions as noted above, electrolysis promotes coagulation of tissue (fulguration) which is a further mechanism of necrosis. In principle, this effect would also occur at the cathode.

FIG. 2 shows the mode of action when the electrode 1 is cathodic and attracts water to a surrounding region L2 by electro-endosmosis. An RF power supply 2 is connected between the electrode 1 and an external conductive pad P which is applied to the patient's skin S. Good electrical contact with the skin S is ensured by applying a conventional conductive gel. A DC potential is applied between electrode 1 and pad P by a DC power supply (not shown) so that a DC path is established through the patient's body.

In use, tissue surrounding electrode 1 is nectrotized by RF ablation and the moisture attracted to the region of the electrode 1 improves both thermal and electrical conductivity and thereby increases the size of the region L2 within which target tissue is necrotized. By the same token surrounding tissue from which water is withdrawn has a lower thermal and electrical conductivity and is protected. Optionally, the DC potential applied between electrode 1 and pad P is sufficient to electrolyze body fluid (which contains sodium ions, chloride ions and hydrogen ions) in the region of electrode 1, so that hydrogen bubbles B are generated. These can be detected by ultrasound imaging to enable the position of electrode 1 to be determined. In principle, the gas bubbles could alternatively be detected by other non invasive imaging means.

In a preferred embodiment of the invention the needle assembly comprises a cannula and at least one said electrode disposed within and extendible from a distal end of said cannula and shaped to penetrate into target tissue. Preferably a plurality of electrodes are disposed within and extendible from the distal end of said cannula and shaped to penetrate into target tissue and are arranged in use to generate electro-osmosis and optionally electrolysis in target tissue in said region. In one embodiment described below the apparatus is a modified version of the LeVeen needle in which a DC biasing potential is applied to the electrode, or to one of the radiating tines, or a separate central tine which extends centrally to lie equidistant to the multiple radial tines. In another embodiment the apparatus comprises a needle with a plurality of electrode loops which can be extended radially outwardly to penetrate tumour tissue (e.g. by virtue either of the radial cutting pressure they apply or of the weakening effect of electrolysis and/or radiofrequency ablation applied in cutting diathermy mode) to form a cage which encloses the tumour.

In certain embodiments, said electrodes are all arranged in use to be biased with the same polarity, said apparatus further comprising means for establishing an electrical connection of opposite polarity with the body of a patient.

Alternatively, one or more of said electrodes are arranged to be biased with one polarity and one or more others of said electrodes are arranged to be biased with the opposite polarity.

In a further variant the apparatus further comprises means for selectively reversing the polarity of one or more of said electrodes.

This embodiment has particular advantages in situations where a tumour is located close to a vein or an artery which would tend to conduct heat away from the tumour. Conventional RF ablation apparatus might not kill a tumour in such a location, but the presence of a vein or an artery would not prevent and indeed might enhance electrolytic necrosis, particularly if the electrode(s) penetrating into the tumour is/are anodically biased so as to discharge chloride ions. More generally, the facility to select the polarity of individual electrodes enables the size and shape of the region of necrosis to be adjusted to match the size and shape of the tumour or other target tissue.

In another embodiment the needle assembly has a lumen in communication with a source of conducting liquid and is arranged to introduce the conducting liquid into said target tissue, said electrode being disposed in said region and arranged to induce electrolysis in said target tissue. In a related embodiment said needle assembly has a lumen communicating with a source of conducting liquid and is arranged to introduce the conducting liquid into said target tissue, said electrode being in electrical contact with said conducting liquid and arranged to induce electro-osmosis in target tissue in said region.

In another aspect the invention provides surgical apparatus for necrotizing target tissue, comprising at least one electrode arranged in use to penetrate into and induce electrolysis in said target tissue and further comprising means for introducing an electrolyte into said target tissue.

Preferably said introducing means communicates with a source of electrolyte, cytocidal substance or precursor thereof, said electrolyte being electrolysible to generate a pharmaceutical agent in situ. For example the pharmaceutical agent can be an anti-tumour compound.

Preferred embodiments will now be described by way of example only with reference to the accompanying drawings wherein:

FIG. 5A is a schematic side elevation of a further needle assembly N' which can be substituted for the needle N of FIG. 3;

FIG. 5B is a schematic side elevation showing the electrode loops of needle N' fully deployed;

FIG. 6 is an end elevation of the needle of FIGS. 5A and 5B showing the cage formed by the fully deployed electrode loops;

FIG. 7 is an axial cross-section taken on VII-VII of FIG. 5A;

Figure 1:
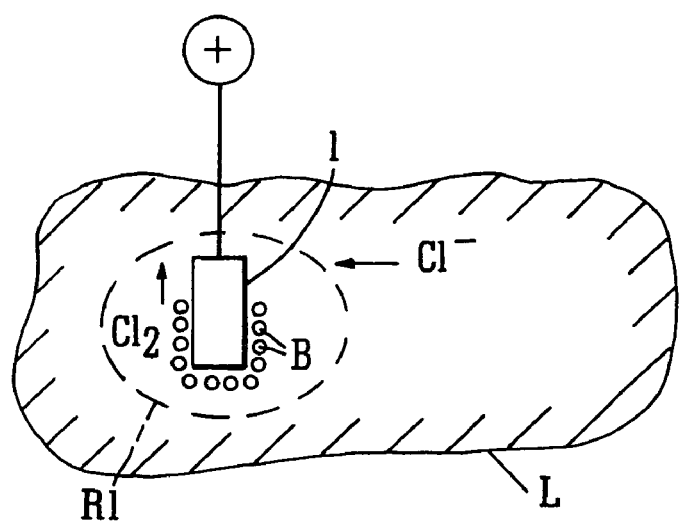
FIG. 1 (already referred to) is a diagrammatic cross section showing the electrolytic effect of an electrode in liver tissue.
Figure 2:
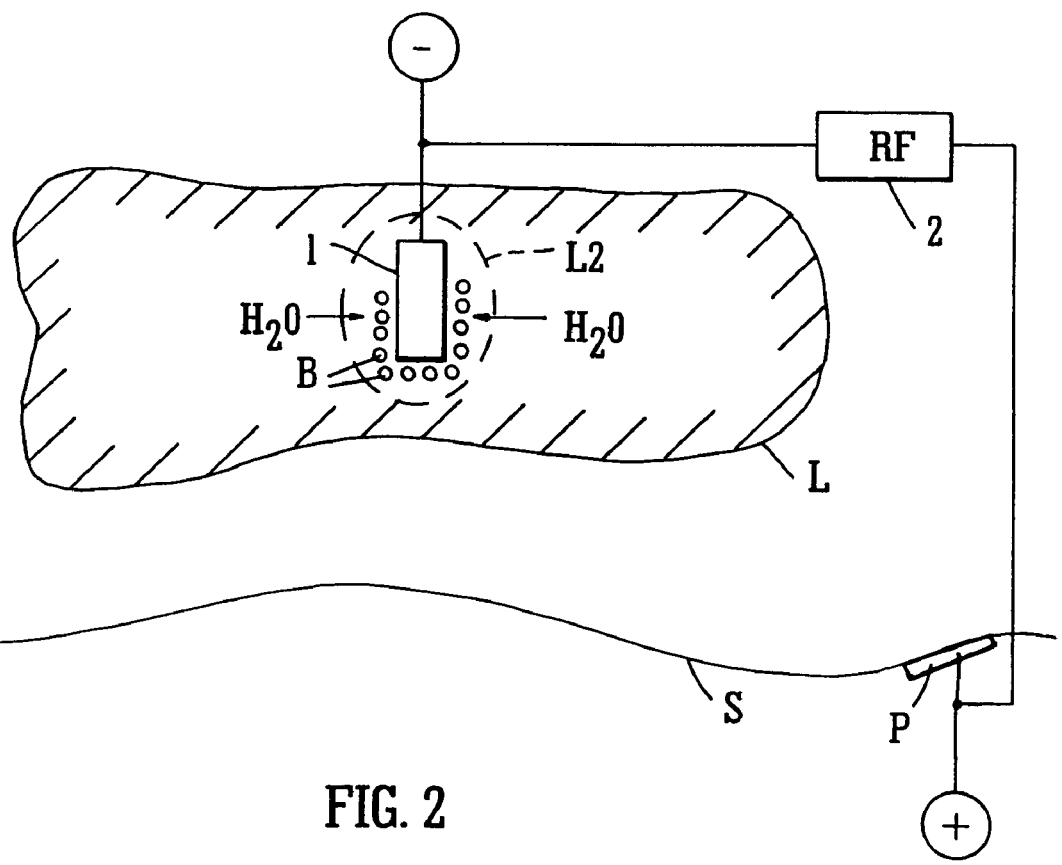
FIG. 2 (already referred to) is a diagrammatic representation showing the electro-osmotic effect of an electrode inserted in liver tissue.
Figure 3:
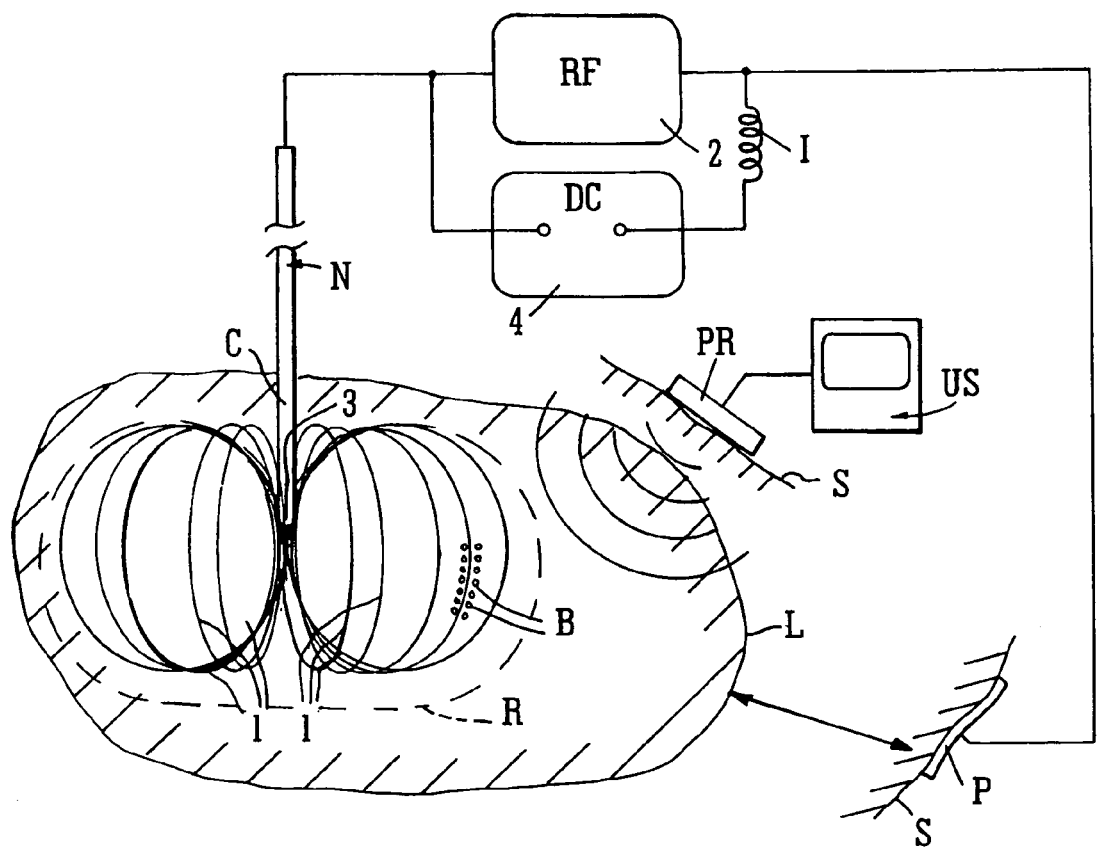
FIG. 3 is a diagrammatic representation of one embodiment of the invention shown inserted into the liver of a patient.

Referring to FIG. 3, a needle assembly N is shown penetrated into the liver L of a patient and comprises a cannula C having a plurality of e.g. ten flexible electrodes 1 extending within its bore from the proximal end to the (lower) distal end thereof and terminating at fixed points 3 near the distal end thereof. Preferably the electrodes 1 are insulated from the cannula C. Prior to insertion, the electrodes 1 are fully withdrawn through the bore of the cannula C so that their end portions are tightly folded over and in contact with its distal rim. In this configuration the cross-section of the needle assembly N is minimized and it can inserted into a desired target region of the patient's liver L. The proximal ends of the electrodes 1 are then pushed through the bore of the cannula to expand into distal loops which extend transversely in a radially distributed array as shown in the Figure.

A conductive pad P is connected to the skin S of the patient and an RF power supply 2 which generates a power of typically 20 to 200 watts at a frequency of 460 kHz is connected between the electrodes 1 and the pad P and is used to ablate the target tissue. A polarizing voltage of e.g. 3 to 9 volts is applied between the pad P and electrodes 1 by a DC power supply 4 and can be switched in polarity. A radio frequency inductor I (of e.g. 1 milliHenry) is connected between one pole of the DC power supply and one pole of the RF power supply in order to prevent short-circuiting of the RF power supply by the DC power supply.

In one mode of operation the electrodes 1 are cathodic and attract water to the surrounding region R, thereby increasing the thermal conductivity and electrical conductivity of the tissue in the region of the electrodes and enhancing the cytocidal effect. In another mode of operation, the polarity is reversed to make the electrodes anodic, discharging chloride ions and generating chlorine which has its own cytocidal effect, in addition to the cytocidal effect of electrolysis.

The bubbles B generated by electrolysis remain close to the electrode 1 before being dispersed in the tissue and thereby define the shape of the electrodes which viewed by an ultrasound imaging system US. This utilises a conventional probe PR applied against the skin S of the patient over the liver L.

In a variant, the electrodes 1 can be insulated from one another and individually connected to selectable poles of a DC power supply, the pad P being omitted. In this variant, the terminals of the RF power supply 2 are connected between different electrodes, as are the terminals of the DC power supply 4, and RF ablation and electro-endosmosis and/or electrolysis occur between selected electrodes 1 or selected groups of electrodes.

After RF ablation has been completed, the cannula C can be temporarily disconnected from the electrodes 1 and a battery can be connected between the skin pad P and the electrodes 1 and worn by the patient to continue electrolytic treatment after the surgical ablation has been completed.

Figure 4:
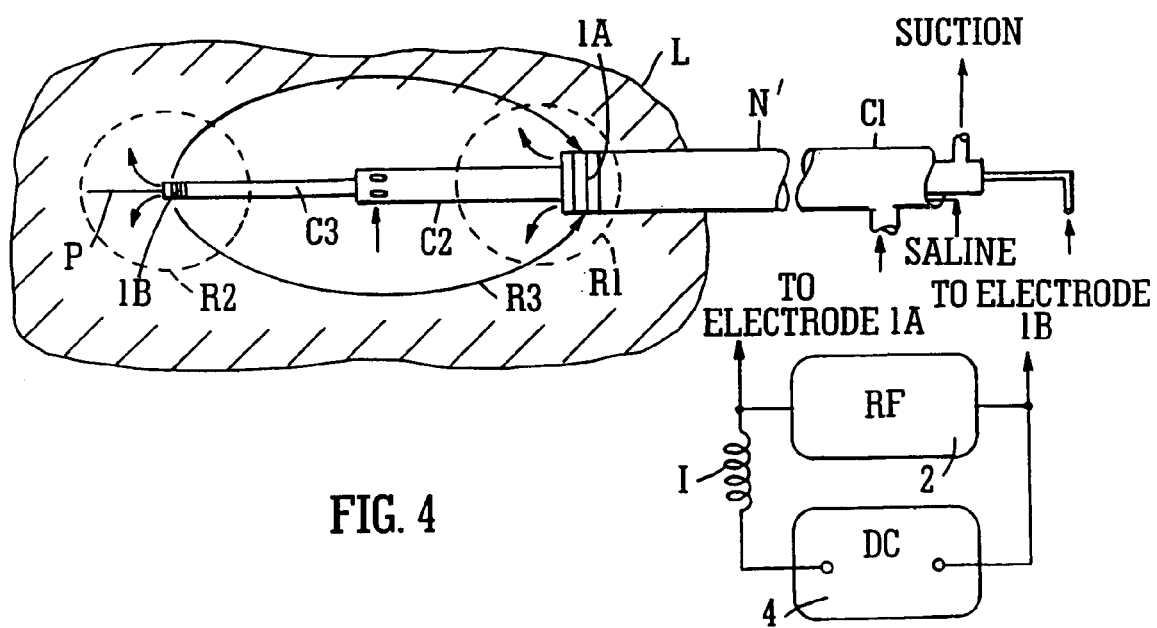
FIG. 4 is a diagrammatic representation of a further embodiment of the invention, again shown inserted into the liver of a patient.

The embodiment of FIG. 4 is a development of the apparatus disclosed in US 2004/0143259 and comprises a needle assembly N' which includes an outer cannula C1, an intermediate cannula C2 and an inner cannula C3. As shown schematically in the Figure, saline solution is injected into the inner cannula C3 and into the passage defined between the outer cannula C1 and the intermediate cannula C2 so as to flow into regions R1 and R2 of the patient's liver L. As shown, a suction communicates with the bore of cannula C2 and suction is applied to remove liquid, solid or gaseous debris (in particular, excess saline solution). A first electrode 1A is disposed on cannula C1 near region R1 and a second electrode 1B is disposed on cannula C3 within region R2. A power supply arrangement similar to that shown in FIG. 3, comprising an RF power supply 2 connected in parallel with a reversible polarity DC power supply 4 is connected between electrodes 1A and 1B (by insulated conductors, not shown, extending through the needle assembly N') and RF ablation occurs in the region R3 between regions R1 and R2. A radiofrequency inductor I (of e.g. 1 milliHenry) is connected between one pole of the DC power supply and one pole of the RF power supply in order to prevent short-circuiting of the RF power supply by the DC power supply. It will be appreciated by persons skilled in the art that the electrodes 1A and 1B are insulated from the needle assembly N'. Electrolytic and/or electro-osmotic effects occur in regions R1 and R2 and enhance the cytocidal effect. In particular, the introduction of saline solution enhances the generation of chlorine in the anodic region.

A thermocouple probe P can be inserted through the lumen of cannula C2 and can be used to detect the temperature in the target tissue and hence to monitor and/or control the power applied by RF power supply 2 in a conventional manner.

FIG. 5A shows a needle assembly N" partly in section and having a barrel portion with eight regularly circumferentially distributed apertures a provided near its sharpened distal tip and eight apertures b similarly disposed near its proximal end, with resilient wire loop electrodes 1 extending longitudinally between each aligned pair of apertures a, b. The distal ends of the wire electrodes are confined within the needle tip and the proximal ends are coupled to the expanded end of an operating rod 10 which terminates in a distal handle 11. Handle 11 is insulated and is slidable within the barrel of the needle assembly and forms a fluid-tight seal therewith.

Preferably a port 12 is provided to inject saline or other electrolyte or cytocidal fluid or precursor thereof solution which in use flows out through apertures a and b.

FIG. 5B shows the handle 11 fully advanced to push the wire electrode loops 1 out of the apertures b to form a cage in the form of a prolate spheroid as shown in FIG. 6. The wire loops are sufficiently thin and stiff to cut tumour tissue as they are expanded radially by advancing handle 11. If necessary this process can be assisted by applying RF ablating power as cutting diathermy and/or DC to lessen the physical resistance of the tissue.

As shown in FIG. 6 a generally spheroidal region R of tumour tissue is enclosed by the resulting electrode cage. This shape is preferable to the doughnut shaped region R enclosed by the electrode configuration of FIG. 3. Electrolysis and ablation (either successive or simultaneous) will have most effect on the periphery of region R and will cut off nutrient channels to its interior, resulting in eventual cell death even in the interior which might not be affected significantly by the RF ablation.

FIG. 7 shows the needle barrel conducting saline solution through its bore around operating rod 10.

Figure 8A:
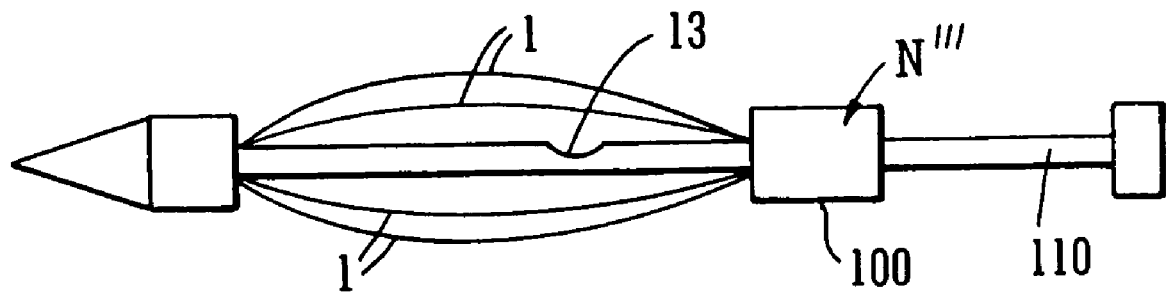
FIG. 8A is a schematic side elevation of a further needle assembly N''' which can be substituted for the needle N of FIG. 3.
Figure 8B:
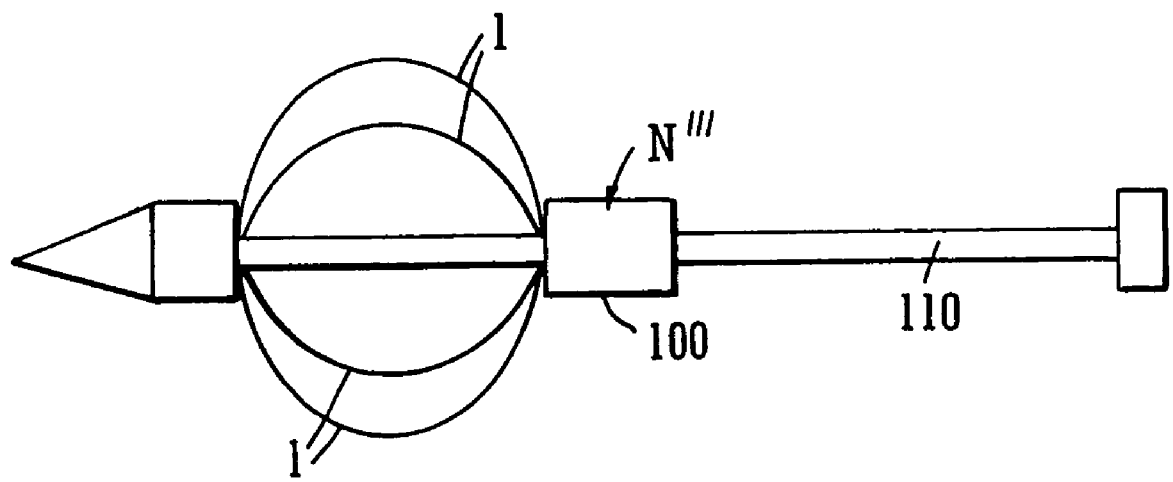
FIG. 8B is a similar schematic side elevation showing the electrode loops of needle N''' fully deployed.

FIG. 8A shows a needle assembly in which a rod 110 having an enlarged sharpened distal tip carries a sliding collar 100. Resilient wire electrode loops 1 extend longitudinally between collar 100 and the rear face of the enlarged distal tip. A locating notch 13 is provided in rod 110 and a complementary resilient interior projection (not shown) in collar 100 engages the notch when the collar is advanced as shown in FIG. 8B. In this configuration the wire electrode loops are compressed and extend radially outwardly to form a cage similar to that formed by the embodiment of FIGS. 5A to 7. Deployment and retraction can be controlled by a motor drive (not shown) coupled to the collar 100 and operation rod 110.

A further adjustable limiting collar can be applied to allow variability in the diameter of the wire cage.

In all the above embodiments, conventional means can be employed to monitor the electrical conductivity of the tissue in order to monitor and/or control the ablation power.

Figure 9:
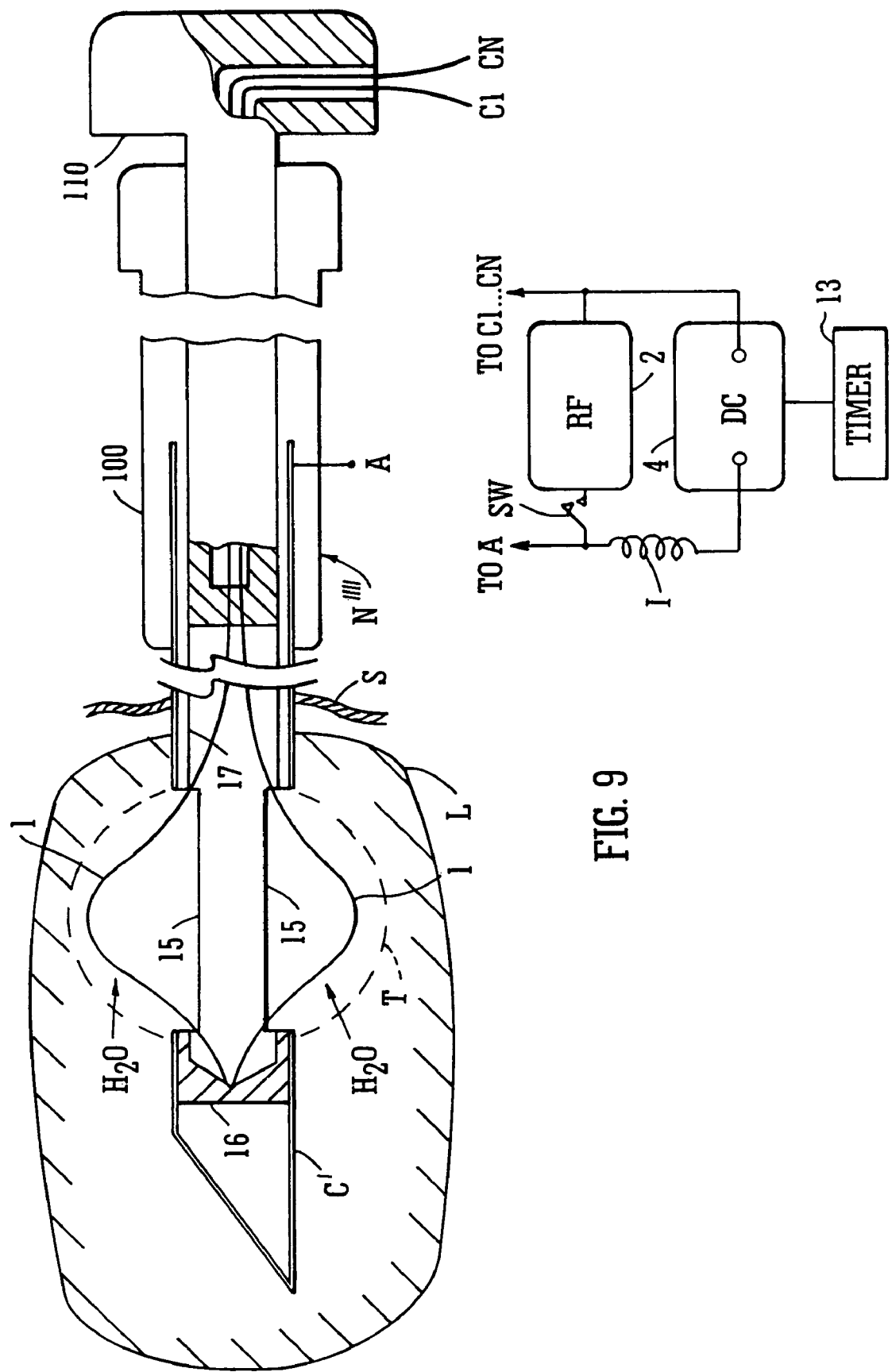
FIG. 9 is a schematic diagram of a further embodiment.

Referring to FIG. 9, a preferred embodiment of the invention is shown, comprising a needle N'''' which comprises an insulating barrel portion 100 in which is inserted a metal cannula portion C' with a sharp tapered distal tip which enables it to penetrate to the skins of a patient and into the liver L or other internal body organ to treat a tumour T therein. The length of the exposed portion of the cannula is suitably 300 mm to 350 mm. The barrel portion 100 has an axial bore 17 therein, which accommodates a plunger 110 having an enlarged handle portion at its proximal end and carrying metallic tines 1 which are embedded in a distal end wall portion of the cannula and accommodated within a axial channel formed therein. The axial channel has a bend formed at the proximal end within the handle portion of the plunger and the tines terminate in contacts C1 . . . Cn. For ease of illustration, only two tines 1 are shown but in practice ten or more tines may be provided. The distal ends of the tines are joined together and bear against a stop 16 formed of insulating material such as PTFE and are electrically isolated from the cannula C' by a sleeve portion of the barrel 100 which extends within the bore of the cannula. A further contact A is led out through the barrel portion 100 from the cannula C'.

As shown, the plunger 110 is shown in a nearly fully extended position (i.e. to the left in the drawing), in which position it forces the tines 1 to bow outwards to form a prolate spheroid corresponding in size and shape to the tumour T. During initial insertion, the plunger 110 is kept in its withdrawn position (i.e. to the right in the drawing) in which the tines 1 are in a relaxed straight configuration and are accommodated within the cannula C'. Axially extending slots 15 are regularly circumferentially distributed about the distal portion of cannula C' in order to accommodate the projection and retraction of the tines 1. Thus each tine extends from and retracts into a respective slot 15.

Both the tines 1 and the cannula C' are suitably made from an inert metal or alloy in order to resist the effects of electrolytic corrosion and for this purpose may be coated with e.g. platinum.

The above contacts C1 . . . Cn of the tines 1 are connected to one output terminal of a parallel-connected combination of RF power supply 2 and a DC power supply 4, the contacts C1 . . . Cn being connected to the negative pole of the DC power supply and the contact A being connected to the positive pole. Thus the tines 1 are cathodic and attract water from the surrounding tissue by electro-endosmosis.

As in the previously described embodiments, an inductor I having a value of 1 milliHenry is connected in series between one pole of the DC power supply 4 and the RF power supply 2 and prevents short circuiting of the RF power supply. Furthermore a switch SW is connected between one pole of the RF power supply and its output connection to cannula contact A and a timer 13 is connected to DC power supply 4.

In use, as stated above the cannula C' is inserted through the skins of a patient and penetrates into the liver or other affected organ to the site of a tumour T with the tines 1 in their retracted condition. The tines 1 are optionally formed of a shaped-memory metal. After insertion, the plunger 110 is depressed to force the tines radially outwardly into the configuration shown in the drawing and DC is applied to the needle from power supply 4 under the control of timer 13. The voltage is suitably in the range 9 to 12 volts and is applied for typically five minutes in order to hydrate the target tissue in the region of the tumour. During this phase, the RF power supply is switched off, i.e. the switch SW is open.

The switch SW is then closed to apply RF power between the tines 1 and exposed metallic portion of cannula C' within the tumour T, causing ablation of the tumour at a power of typically 20 watts. This phase is terminated when the detected impedance as sensed by the needles reaches a predetermined value e.g. 999 ohms, indicating that ablation has been substantially completed. During this phase, the DC power supply 4 remains energized. When ablation has been completed, the plunger 110 is retracted (i.e. moved to the right in the drawing) to retract the tines 1 and the instrument is withdrawn from the patients body.

In a variant, the tines 1 could be insulated from one another and RF and/or DC could be applied selectively to different tines. In a further variant, the biasing potential provided by the DC power supply 4 could be applied between different insulated tines rather than between a set of tines and the cannula C' as described above.

In the above described preferred embodiments of the invention, the cathode is also coupled to an AC power supply and is arranged to necrotize target tissue by diathermal ablation. However as noted above other modes of energy transfer, eg laser, microwave or other heating/desiccating means may be employed to ablate the target tissue.

We claim:

1. Surgical apparatus for treating tumours in internal organs or bones of a human patient, the apparatus comprising a penetrative needle assembly for penetrating into an internal organ or bone of the human patient and ablating tumour tissue therein, said penetrative needle assembly comprising at least one cathode in an ablation zone of the needle assembly for hydrating, by electro-endosmosis, target tumour tissue in the ablation zone, an AC source coupled to the penetrative needle assembly for supplying ablating power of at least 5 W thereto, a DC source for biasing said cathode to a negative potential to induce said electro-endosmosis, wherein said AC source and said DC source are provided with switching means for inducing said electro-endosmosis prior to or simultaneously with ablating said tumour tissue in the ablation zone.

2. Surgical apparatus according to claim 1, wherein said apparatus further comprises means for establishing an electrical connection of positive polarity with the body of the patient.

3. Surgical apparatus according to claim 1, further comprising an anode for insertion into the patient's body tissue.

4. Surgical apparatus according to claim 1, wherein said anode is in the form of a needle.

5. Surgical apparatus according to claim 1, wherein said negative potential is in the range −9V to −12V relative to a positive pole of said DC source.

6. Surgical apparatus according to claim 1, comprising means for applying an initial treatment phase in which said cathode is biased to a negative potential to induce electro-endosmosis and for applying a subsequent treatment phase in which said energy transfer means is activated to ablate target tumour tissue hydrated in the initial treatment phase.

7. Surgical apparatus according to claim 1, wherein said needle assembly comprises a cannula and at least one said cathode disposed within and extendable from a distal end of said cannula and shaped to penetrate into target tissue.

8. Surgical apparatus according to claim 1, wherein a plurality of electrodes for inducing electro-endosmosis in target tumour tissue in said region are disposed within and extendable from the distal end of said cannula.

9. Surgical apparatus according to claim 1, wherein said penetrative needle assembly comprises a plurality of electrodes, wherein all said electrodes are biased with negative polarity.

10. Surgical apparatus according to claim 1, wherein said needle assembly has a lumen communicating with a source of conducting liquid or cytocidal substance or precursor thereof for introducing the conducting liquid or substance into said target tumour tissue, said cathode being in electrical contact with said conducting liquid or substance for inducing electro-endosmosis in target tissue in said zone.

11. Surgical apparatus according to claim 10, wherein said needle arrangement has a further lumen and further comprising extraction means in communication with said further lumen for extracting liquid, solid or gaseous debris from said target tissue.

12. Surgical apparatus according to claim 1, which includes means for generating electrolysis in said zone.

13. Surgical apparatus according to claim 12, wherein said apparatus further comprises ultrasonic imaging means for detecting electrolytically-produced gases in said zone.

14. Surgical apparatus according to claim 13, wherein said ultrasonic imaging means is a Doppler ultrasound imager.

15. Surgical apparatus according to claim 1, wherein said needle assembly comprises an extendable electrode array enclosing a volume of tumour tissue for selective ablation of a periphery of said volume of tumour tissue.

16. Surgical apparatus according to claim 1, wherein said AC source is an RF ablation power supply.

17. A method of treatment of a tumour in an organ or bone of a human or an animal body, the method comprising (a) providing the surgical apparatus of claim 1; and (b) applying the apparatus to the human or animal body to induce electro-endosmosis in and hydrate target tumour tissue of the human or animal body in the ablation zone and subsequently or simultaneously to ablate the target tumour tissue in the ablation zone.

18. A method according to claim 17, wherein the electro-endosmosis is induced prior to ablating the target tumour tissue.

19. A method according to claim 17, wherein the electro-endosmosis is induced for a period of 60 to 600 seconds prior to ablating the target tumour tissue.

20. A method according to claim 17, wherein the electro-endosmosis is induced for a period of 120 to 400 seconds prior to ablating the target tumour tissue.

21. A method according to claim 17, wherein the electro-endosmosis is induced for a period of 240 to 360 seconds prior to ablating the target tumour tissue.

22. A method according to claim 17 wherein the electro-endosmosis is induced by applying a DC potential between an external conductive pad and the cathode of the penetrative needle assembly, the external conductive pad being in contact with the skin of the human or animal body.

23. A method according to claim 17 wherein the electro-endosmosis is induced by applying a DC potential between an anodic electrode and the cathode of the penetrative needle assembly, the anodic electrode being inserted into the human or animal body and being spaced apart from the penetrative needle assembly.

24. A method according to claim 17 wherein said needle assembly comprises an extended electrode array enclosing a volume of tumour tissue and a periphery of said volume is ablated.

25. A method according to claim 17 wherein said organ is a liver.

26. A method according to claim 17 wherein a negative DC potential sufficient to generate gas bubbles by electrolysis is applied to said penetrative needle assembly and said gas bubbles are detected by ultrasonic imaging.

27. A method according to claim 17 wherein said target tumour tissue is ablated with a power of at least 5 W.

28. A method according to claim 17 wherein said target tumour tissue is ablated with a power of at least 10 W.

29. A method according to claim 17 wherein said target tumour tissue is ablated with a power of at least 20 W.

* * * * *